(12) United States Patent
Wachter et al.

(10) Patent No.: US 6,248,313 B1
(45) Date of Patent: *Jun. 19, 2001

(54) HAIR COSMETIC PREPARATIONS CONTAINING CATIONIC BIOPOLYMERS

(75) Inventors: Rolf Wachter, Duesseldorf; Joerg Kahre; Matthias Hofmann, both of Monheim; Michael Heyer, Erkrath, all of (DE)

(73) Assignee: Henkel Kommanditgesellschaft auf Aktien, Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,530

(22) PCT Filed: Jun. 24, 1996

(86) PCT No.: PCT/EP96/02733

§ 371 Date: Feb. 24, 1998

§ 102(e) Date: Feb. 24, 1998

(87) PCT Pub. No.: WO97/02007

PCT Pub. Date: Jan. 23, 1997

(30) Foreign Application Priority Data

Jul. 3, 1995 (DE) .............................................. 195 24 125

(51) Int. Cl.[7] ................. A61K 7/06; A61K 7/11
(52) U.S. Cl. ................. 424/70.1; 424/70.11; 424/70.13; 424/70.15
(58) Field of Search ................. 424/70.1, 70.11, 424/70.13, 70.15

(56) References Cited

U.S. PATENT DOCUMENTS

| | | | |
|---|---|---|---|
| 4,134,412 | 1/1979 | Gross et al. | 132/7 |
| 4,172,887 | 10/1979 | Vanlerberghe et al. | 424/70 |
| 4,772,689 | 9/1988 | Lang et al. | 536/20 |
| 4,845,204 | 7/1989 | Lang et al. | 536/20 |
| 5,420,197 | 5/1995 | Lorenz et al. | 525/54.3 |
| 5,442,048 | 8/1995 | Meister et al. | 536/20 |
| 5,512,276 | * 4/1996 | Lang et al. | 424/70.11 |
| 5,525,332 | * 6/1996 | Gough et al. | 425/70.12 |
| 5,690,924 | * 11/1997 | Keil et al. | 429/78.03 |

FOREIGN PATENT DOCUMENTS

| | | |
|---|---|---|
| 26 27 419 | 12/1977 | (DE) . |
| 35 01 891 | 7/1986 | (DE) . |
| 35 04 095 | 8/1986 | (DE) . |
| 0 272 472 | 6/1988 | (EP) . |
| 0 382 150 | 8/1990 | (EP) . |
| 2 252 840 | 6/1975 | (FR) . |
| 2 063 671 | 6/1981 | (GB) . |
| 6-100419 | 4/1994 | (JP) . |
| 408040843A | * 8/1994 | (JP) ................. A61K/7/06 |
| WO91/05808 | 5/1991 | (WO) . |

OTHER PUBLICATIONS

Parfumerie und Kosmetik vol. 64 (7): 367–371 (1983).

HAPPI 27: 57 (1990).

Drug Cosm. Ind. 148:24 (1991).

Seifen–Öle–Fette–Wachse 117:633 (1991).

"Kosmetische Färbemittel" Farbstoffkommission der Deutschen Forschungsgemeinschaft, Verlag Chemie, Weinheim, pp. 81–106 (1984).

* cited by examiner

*Primary Examiner*—Thurman K. Page
*Assistant Examiner*—S. Tran
(74) *Attorney, Agent, or Firm*—John E. Drach; Glenn E. Murphy; Steven J. Trzaska

(57) ABSTRACT

A hair cosmetic formulation containing a cationic bipolymer and a polyvinylpyrrolidone/viny acetate copolymer in a weight ratio from 1:10 to 1:50.

8 Claims, No Drawings

HAIR COSMETIC PREPARATIONS CONTAINING CATIONIC BIOPOLYMERS

This application is a 371 PCT/EP96/02733 Jun. 24, 1996.

FIELD OF THE INVENTION

This invention relates to hair-cosmetic formulations with improved film-forming properties containing cationic biopolymers and polyvinyl pyrrolidone/vinyl acetate copolymers in selected mixing ratios and to the use of the cationic biopolymers for improving the film-forming properties of the said copolymers.

1. Prior Art

Hair-cosmetic formulations, for example lacquers or styling preparations, set through the presence of polymers, preferably of the polyvinyl pyrrolidone/vinyl acetate type, which are absorbed by the keratin fibers and provide them with the required hold. However, the disadvantage of these polymers is that, after repeated application, the films become brittle on drying so that not only is the styling effect lost, the hair can also be damaged.

Accordingly, the problem addressed by the present invention was to provide cosmetic formulations which, although containing polyvinyl pyrrolidone/vinyl acetate copolymers as film formers, would have a significantly reduced tendency towards stress cracking for at least the same film hardness.

2. Description of the Invention

The present invention relates to hair-cosmetic formulations containing
 a) cationic biopolymers and
 b) polyvinyl pyrrolidone/vinyl acetate copolymers in a ratio by weight of 1:5 to 1:50.

It has surprisingly been found that the addition of even very small quantities of cationic biopolymers to polyvinyl pyrrolidone/vinyl acetate copolymers, whose film-forming properties are individually known, has a moisture-regulating effect and synergistically reduces the tendency towards stress cracking without any adverse effect on film hardness. In view of the fact that the cationic biopolymers are very costly to produce and are therefore expensive, the possibility of significantly improving the performance properties of the copolymers by adding very small quantities also represents a particular economic advantage.

Cationic biopolymers

According to the invention, particularly suitable cationic biopolymers for component a) are hydrocolloids of the chitosan type. Chemically, they are partly deacetylated chitins varying in molecular weight which contain the idealized monomer unit (I):

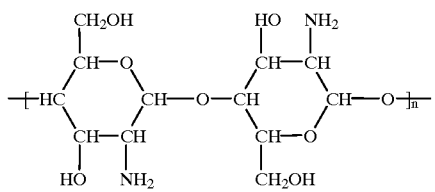

In contrast to most hydrocolloids, which are negatively charged at biological pH values, chitosans are cationic biopolymers under these conditions. The positively charged chitosans are capable of interacting with oppositely charged surfaces and, accordingly, are used in cosmetic hair-care and body-care formulations, for example as film formers.

Besides chitosans, quaternized, alkylated and/or hydroxyalkylated derivatives, optionally in microcrystalline form, may also be used. The chitosans and their derivatives are generally used in the form of aqueous gels with a solids content of 1 to 5% by weight.

Reviews on this subject have been published, for example, by B. Gesslein et al. in HAPPI 27, 57 (1990), by O. Skaugrud in Drug Cosm. Ind. 148, 24 (1991) and by E. Onsoyen et al. in Seifen-Öle-Fette-Wachse 117, 633 (1991).

Chitosans are produced from chitin, preferably from the shell remains of crustaceans which are available in large quantities as inexpensive raw materials. Normally, the chitin is first deproteinized by addition of bases, demineralized by addition of mineral acids and, finally, deacetylated by addition of strong bases, the molecular weights being spread over a broad range. Corresponding processes for the production of—microcrystalline-chitosan are described, for example, in WO 91/05808 (Firextra Oy) and in EP-B1 0 382 150 (Hoechst).

One preferred embodiment of the invention is characterized by the use of particularly low-ash cationic biopolymers which are obtained by (a) treating fresh crustacean shells with dilute aqueous mineral acid,
 (b) treating the resulting demineralized first intermediate product with aqueous alkali metal hydroxide solution,
 (c) treating the resulting lightly deproteinized second intermediate product with more dilute aqueous mineral acid,
 (d) finally treating the resulting decalcified third intermediate product with concentrated aqueous alkali metal hydroxide and deacetylating it to a content of 0.05 to 0.5 and, more particularly, 0.15 to 0.25 mole acetamide per mole monomer unit and
 (e) optionally carrying out a pressure/heat aftertreatment to adjust the viscosity.

Polyvinyl pyrrolidone/vinyl acetate copolymers

Polyvinyl pyrrolidone/vinyl acetate copolymers (PVP/VA), which form component b), represent known protective colloids for cosmetic applications which are marketed, for example, under the name of Luviskol® by BASF AG of Ludwigshafen. FRG. The copolymers are normally used in the form of aqueous solutions with a solids content of 1.5 to 30% by weight. The formulations may contain components a) and b) in a ratio by weight (based on dry matter) of 1:5 to 1:50, preferably 1:10 to 1:45 and more preferably 1:30 to 1:40.

Commercial Applications

Mixtures of cationic biopolymers and polyvinyl pyrrolidone/vinyl acetate copolymers show improved film-forming properties. Accordingly, the present invention also relates to the use of cationic biopolymers as additives for improving the film-forming properties of polyvinyl pyrrolidone/vinyl acetate copolymers.

Hair-cosmetic formulations

The formulations according to the invention may contain surfactants, emulsifiers, superfatting agents, thickeners, cationic polymers, silicone compounds, biogenic agents, film formers, preservatives, dyes and perfumes as further auxiliaries and additives.

Typical examples of suitable surfactants are fatty alcohol polyglycol ether sulfates, monoglyceride sulfates, mono- and/or dialkyl sulfosuccinates, fatty acid isethionates, fatty acid sarcosinates, fatty acid taurides, ether carboxylic acids, alkyl oligoglucosides, fatty acid glucamides, alkylamidobetaines and/or vegetable protein fatty acid condensates.

Suitable emulsifies are both known w/o and o/w emulsifiers such as, for example, hydrogenated and ethoxylated castor oil, polyglycerol fatty acid esters or polyglycerol polyricinoleates or polyglycerol poly-12-hydroxystearates.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose; relatively high molecular weight polyethylene glycol monoesters and diesters of fatty acids, polyacrylates, polyvinyl alcohol and polyvinyl pyrrolidone; surfactants such as, for example, narrow-range fatty alcohol ethoxylates or alkyl oligoglucosides; and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryidimonium Hydroxypropyl Hydrolyzed Collagen (Lamequat®L, Grünau GmbH), polyethyleneimine, cationic silicone polymers such as, for example, Amidomethicone or Dow Corning 929, Dow Corning Co., USA, copolymers of adipic acid and dimethylaminohydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkyl-modified silicone compounds. In the context of the invention, biogenic agents are, for example, plant extracts and vitamin complexes. Suitable preservatives are, for example, phenoxyethanol, formaldehyde solution, parabens, pentadiol or sorbic acid. Suitable pearlescers are, for example, glycol distearic acid esters, such as ethylene glycol distearate, and also fatty acid monoglycol esters. The dyes used may be selected from any of the substances which are licensed and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total percentage content of auxiliaries and additives may be 1 to 50% by weight and is preferably 5 to 40% by weight, based on the formulation.

EXAMPLES

Film hardness. Film hardness was determined using the measuring arrangement for determining König pendulum hardness (seconds pendulum hardness at 6° deflection; instrument Erichsen 299/300, Hermer/Sundvig) which reproduces the hardness of a lacquer film as the measurement result. To this end, 1 % by weight solutions of a chitosan (Hydagen® CMF, Henkel KGaA, Düsseldorf, FRG), a polyvinyl pyrrolidone/vinyl acetate copolymer (Luviskol® VA 64, BASF AG) and a mixture in a ratio by weight of a) to b) of 1:40 were applied to a slide and air-dried. The procedure was repeated several times until a 30 μm thick dried film was obtained. The measurement was carried out by placing a pendulum on the film and causing it to oscillate with a constant initial deflection. To determine the measurement result, the number of pendulum deflections up to the minimal deflection was counted and multiplied by the oscillation time (1.4). The results are set out in Table 1:

TABLE 1

Determination of pendulum hardness

| Example. | Starting material | Pendulum hardness |
|---|---|---|
| C1 | Chitosan | 149 |
| C2 | PVP/VA | 148 |
| 1 | Chitosan:PVP/VA = 1:40 | 148 |

It can be seen that the hardness of the film is not adversely affected by the addition of chitosan to the PVP/VA copolymer.

Stress cracking. To determine stress cracking, films with a layer thickness of about 30 μm were examined under a microscope after drying. PVP/VA copolymers with a solids content of 1.5 to 30% by weight and various mixtures of chitosan gel (1% by weight solids content) and a PVP/VA solution (solids content 2.0% by weight) were used. The results are set out in Table 2.

TABLE 2

Stress cracking

| Example | Starting material | Appearance of the dried films |
|---|---|---|
| C4 | PVP/VA solution (1.5%) | Fine stress cracks throughout |
| C5 | PVP/VA solution (2.0%) | Fine stress cracks throughout |
| C6 | PVP/VA solution (30.0%) | Large stress cracks throughout |
| 2 | Chitosan:PVP/VA = 1:10 | Hardly any stress cracks |
| 3 | Chitosan:PVP/VA = 1:20 | Hardly any stress cracks |
| 4 | Chitosan:PVP/VA = 1:40 | Hardly any stress cracks |
| 5 | Chitosan:PVP/VA = 1:50 | Hardly any stress cracks |

What is claimed is:

1. A hair cosmetic formulation comprising a cationic biopolymer selected from the group consisting of chitosans, quaternized chitosans, alkylated chitosans, and hydroxyalkylated chitosans; and a polyvinylpyrrolidone/vinyl acetate copolymer in a weight ratio of 1:10 to 1:50.

2. A method of improving the film-forming properties of a polyvinylpyrrolidone/vinyl acetate copolymer in a hair cosmetic formulation by adding to a hair cosmetic formulation containing a polyvinylpyrrolidone/vinyl acetate copolymer a cationic biopolymer the weight ratio of cationic biopolymer selected from the group consisting of chitosans, quaternized chitosans, alkylated chitosans, and hydroxyalkylated chitosans, wherein to polyvinylpyrrolidone/vinyl acetate copolymer is 1:10 to 1:50.

3. A hair cosmetic formulation according to claim 1, wherein the weight ratio of cationic biopolymer to polyvinylpyrrolidone/vinyl acetate copolymer is 1:10 to 1:45.

4. A hair cosmetic formulation according to claim 3, wherein the weight ratio of cationic biopolymer to polyvinylpyrrolidone/vinyl acetate copolymer is 1:30 to 1:40.

5. A hair cosmetic formulation comprising chitosan and a polyvinylpyrrolidone/vinyl acetate copolymer in a weight ratio of 1:5 to 1:50.

6. A method of improving the film-forming properties of a polyvinylpyrrolidone/vinyl acetate copolymer in a hair cosmetic formulation by adding to a hair cosmetic formulation containing a polyvinylpyrrolidone/vinyl acetate copolymer an amount of chitosan such that the weight ratio of chitosan to polyvinylpyrrolidone/vinyl acetate copolymer is 1:5 to 1:50.

7. A hair cosmetic formulation according to claim 5, wherein the weight ratio of chitosan to polyvinylpyrrolidone/vinyl acetate copolymer is 1:10 to 1:45.

8. A hair cosmetic formulation according to claim 7, wherein the weight ratio of cationic biopolymer to polyvinylpyrrolidone/vinyl acetate copolymer is 1:30 to 1:40.

* * * * *